(12) United States Patent
Wei

(10) Patent No.: US 8,476,317 B2
(45) Date of Patent: *Jul. 2, 2013

(54) N-ALKYLCARBONYL-AMINO ACID ESTER COMPOUNDS AND THEIR USE FOR COUGH AND PHARYNGITIS

(76) Inventor: Edward Tak Wei, Berkeley, CA (US)

( * ) Notice: Subject to any disclaimer, the term of this patent is extended or adjusted under 35 U.S.C. 154(b) by 156 days.

This patent is subject to a terminal disclaimer.

(21) Appl. No.: 12/930,825

(22) Filed: Jan. 18, 2011

(65) Prior Publication Data

US 2012/0184614 A1   Jul. 19, 2012

(51) Int. Cl.
*A61K 31/215* (2006.01)
(52) U.S. Cl.
USPC .......................................... 514/529
(58) Field of Classification Search
None
See application file for complete search history.

*Primary Examiner* — Craig Ricci

(57) ABSTRACT

The present invention generally relates to refreshing, soothing, and cooling compounds that affect sensory processes. More particularly, the present invention pertains to certain N-alkylcarbonyl-amino acid esters compounds as described herein; compositions and articles comprising such compounds; and methods of treatment, for example, methods of reducing cough and pharyngeal irritation, itch, and/or pain.

1 Claim, 1 Drawing Sheet

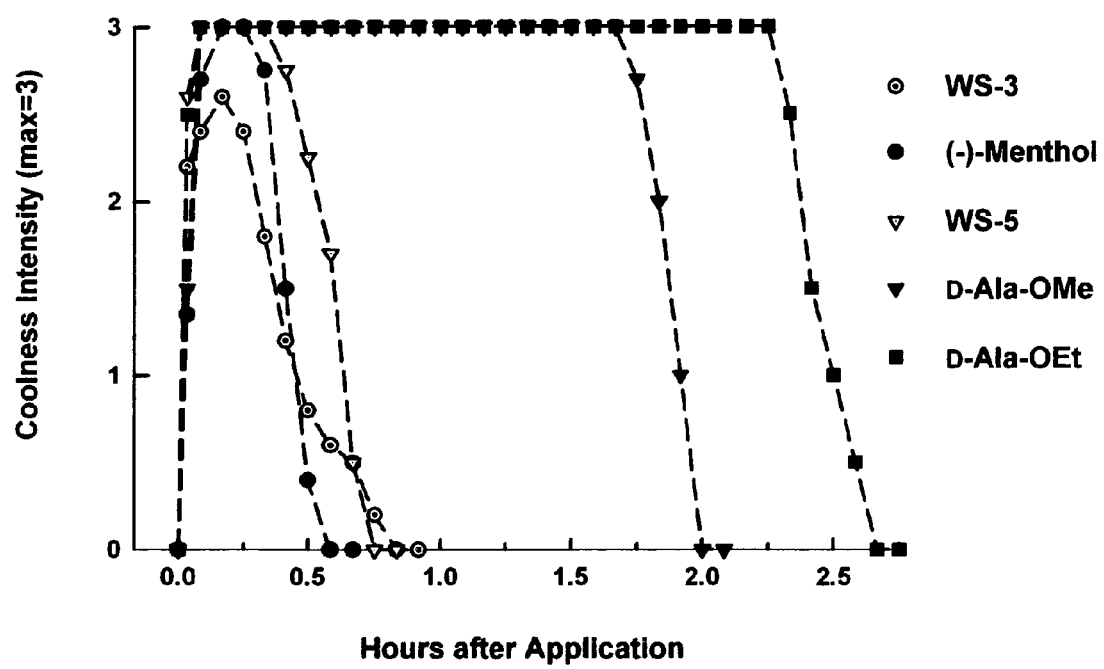

N-ALKYLCARBONYL-AMINO ACID ESTER COMPOUNDS AND THEIR USE FOR COUGH AND PHARYNGITIS

RELATED APPLICATIONS

This application is a continuation-in-part of U.S. patent application 20080227857, filed Mar. 23, 2006, inventor Wei, entitled "N-Alkylcarbonyl-Amino Acid Ester and N-Alkylcarbonyl-Amino Lactone Compounds and Their Use", incorporated by reference.

RELATED APPLICATIONS

This application is related to:

U.S. Provisional Application No. 60/667,166 filed 29 Mar. 2005;

U.S. Provisional Application No. 60/683,384 filed 20 May 2005;

U.S. Provisional Application No. 60/702,505 filed 26 Jul. 2005;

U.S. patent application Ser. No. 11/203,728 filed 13 Aug. 2005; and

U.S. Provisional Application No. 60/772,374 filed 9 Feb. 2006; the contents of each of which are incorporated herein by reference in their entirety.

TECHNICAL FIELD

The present invention generally relates to refreshing, soothing, and cooling compounds that affect sensory processes. More particularly, the present invention pertains to certain N-alkylcarbonyl-amino acid ester compounds; compositions and articles comprising such compounds; and methods of treatment, for example, methods of alleviating the discomforts of irritation, itch, and pain in the linings of the oral cavity, pharynx, and upper respiratory tract, for example, in methods of treatment of cough and/or asthma.

BACKGROUND

Menthol and menthol-like compounds are used in toiletries, confectionery, comestibles, and over-the-counter medications as ingredients to refresh, cool, flavor, counter-irritate, and anesthetize the skin and mucous membranes of the mouth and upper airways. Menthol's utility in relief of sensory discomfort is, however, limited by its short duration of action and by its multimodal actions on sensory processes—including odor, harshness of taste, and irritation. Menthol can relieve nasal congestion and suppress cough—but the effect, especially for cough, is transient, and the irritant properties of mucous membranes limit the use of higher dosage.

Current medications for cough include dextromethorphan, codeine, and menthol. These methods and compounds have moderate effectiveness and ease of use. There is a need for compounds like menthol that refresh, cool, and soothe the oral cavity and throat, but without the disadvantages of odor, irritancy, and a short duration of action. In order to treat medically important discomforts of sustained coughing, it is important to have compounds that act longer than menthol.

About three decades ago, a group of scientists synthesized over 1200 compounds in an attempt to find cooling agents that had properties better than menthol. Their results were summarized in a paper (Watson et al., "New compounds with the menthol cooling effect," J. Soc. Cosmet. Chem., 29: 185-200, 1978). From this research, an N-alkyl-cycloalkyl- and an N-alkyl-alkyl carboxamide, WS-3, WS-5, and WS-23, were brought to the market and are used as additives for confectionery, comestibles, (e.g., candy, chewing gum), and toiletries. A new ingredient for cough has not been discovered.

In U.S. Pat. No. 4,178,459 (11 Dec. 1979), Watson et al. described cooling properties of some N-alkoxycarbonylalkyl-substituted p-menthane-carboxamides. The designation in '459 is silent with respect to stereoisomerism on the alanine moiety of alanyl O-esters. The recent information on cooling agents used for topical applications was reviewed by M. B. Erman ("Cooling agents and skin care applications," Cosmetics & Toiletries, 120: 105-118, May 2005; "Progress in physiological cooling agents," Perfumer & Flavorist, 29: 34-50, 2004) and by P. Jacobs and W. Johncock ("Some like it cool," Parfumerie and Kosmetik, 80: 26-31, 1999).

None of the menthol-like compounds currently known to the art have the potency or duration of action to qualify them as possible medications for use in ailments such as cough and pharyngitis.

SUMMARY OF THE INVENTION

One aspect of the present invention pertains to certain N-alkylcarbonyl-amino acid ester compounds, as described herein.

Another aspect of the invention pertains to a composition comprising such a compound and a delivery vehicle (e.g., for delivering the compound to a human).

In one embodiment, the delivery vehicle is a pharmaceutically acceptable carrier or diluent.

In one embodiment, the delivery vehicle is adapted to deliver the compound to the oropharynx.

In one embodiment, the delivery vehicle is a orally disintegrating tablet composed of a sugar matrix.

In one embodiment, the delivery vehicle is adapted to deliver the compound to the oropharynx and/or the upper respiratory tract of the human.

In one embodiment, the compound is present in the composition in an amount of 1 to 10 mg, for example, in a rapidly orally disintegrating tablet.

Another aspect of the present invention pertains to methods of treatment of the ororpharynx, or upper airways of a human, comprising:

contacting a composition comprising such a compound and a delivery vehicle with the oropharyngeal surface, or upper airways of the human, thereby delivering an effective amount of the compound to the mucous membranes of the human.

Another aspect of the present invention pertains to methods of treatment of a condition, comprising:

contacting a composition comprising a compound according to any one of claims and a delivery vehicle with, e.g., the oropharynx or upper airways of the human, thereby delivering an amount of the compound therapeutically effective for treatment of (e.g., alleviation of) the condition.

Another aspect of the present invention pertains to such a compound for use in a method of treatment of the human or animal body by therapy.

Another aspect of the present invention pertains to use of such a compound in the manufacture of a medicament for use in a method of treatment.

In one embodiment, the treatment is treatment of (e.g., alleviation of) cough and/or the sense of irritation and/or obstruction of the upper airways (e.g., wherein the contacting delivers an amount of the compound that is therapeutically effective for alleviation of cough and/or the sense of irritation and/or obstruction of the upper airways).

In one embodiment, the treatment is treatment of cough (e.g., wherein the contacting delivers an amount of the compound that is therapeutically effective for treatment of cough).

In one embodiment, the treatment is smoking cessation therapy (e.g., wherein the contacting delivers an amount of the compound that is effective in smoking cessation therapy).

In one embodiment, the treatment is treatment to reduce host dissemination of an infectious microorganism (e.g., wherein the contacting delivers an amount of the compound that is effective to reduce host dissemination of an infectious microorganism).

In one embodiment, the treatment is treatment to prevent coughing and airborne transmission of an infectious microorganism (e.g., wherein the contacting delivers an amount of the compound that is effective to prevent coughing and airborne transmission of an infectious microorganism).

As will be appreciated by one of skilled in the art, features and preferred embodiments of one aspect of the invention will also pertain to other aspect of the invention.

Other advantages and aspects of the invention will be understood by reading the following detailed description and the accompanying claims.

BRIEF DESCRIPTION OF THE DRAWINGS

FIG. 1 is a graph showing duration of cooling (hours) for five compounds (in order, left to right): WS-3, (−)-menthol, WS-5, D-Ala-OMe, and D-Ala-OEt. The durations of cooling effects of known agents in commerce, e.g., (−)-menthol, WS-3, and WS-5, are ≦0.5 hr, and relatively short compared to the D-Ala-OMe and D-Ala-OEt of >1.5 hr. The presence the D-Ala configuration increases duration of action and these two D-Ala compounds are examples of the preferred embodiments of this invention.

DETAILED DESCRIPTION

A class of compounds that is suitable to be used as an active ingredient in (e.g., pharmaceutical) preparations for use on the mucous membranes of the oropharynx and upper respiratory tract has been found.

These compounds are suitable, for example, for use as therapeutic agents, to reduce discomfort such as irritation, itch and pain in the lining of the pharynx and to reduce cough.

These compounds have one or more of the following properties:

- a refreshing, soothing, and cooling action on surfaces of the oropharynx and/or throat, and, in pathological states, exert an anti-irritant, anti-pruritic, anti-tussive, and/or anti-nociceptive effect;
- a rapid onset of action of less than about 5 minutes (e.g., from 0.5 to 5 minutes), preferably less than about 3 minutes (e.g., from 0.5 to 3 minutes) for example, when delivered onto the oropharynx at 2 to 10 mg per dose.
- a duration of action that exceeds 1 hour
- wherein repeat applications do not result in altered sensitivity; and
- a potent cool, soothing, and refreshing sensation when applied onto the oropharynx that counteracts irritative stimuli in the throat that causes cough and wheezing.

These compounds are shown in Formula 1.

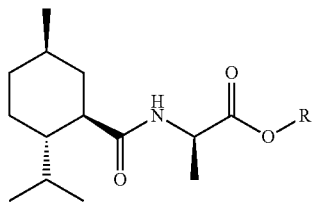

Formula (1)

wherein:
R is methyl, ethyl, or isopropyl

The D-configuration has the effect of increasing potency and duration of action, and of producing a selective refreshing coolness with the absence of tissue irritation.

The preferred compounds are shown as No. 1, No. 2, and No. 3 in Table 1. In the text of this application, compounds will be identified by the No. in Table 1 or by an abbreviation derived from the nature of ester, e.g. D-Ala-OEt as being equal to No. 2, without specifying that the amino acid ester is further attached to the p-menthoyl moiety [(R)-2-[((1R,2S, 5R)-2-isopropyl-5-methyl-cyclohexanecarbonyl)-].

The compounds of Formula 1, designated long-acting N-alkylcarbonyl amino acid esters (NACE) are distinguished from other N-alkylcarbonyl-amino acid esters (e.g., WS-5 and WS-31) and N-alkyl substituted carboxamides (e.g., WS-3, WS-12, WS-23) which are known to have cooling properties and the two (WS-3 and WS-23) that are commercially used in comestibles, confectionery, and toiletries.

TABLE 1

Preferred embodiments of this discovery.

| | | | |
|---|---|---|---|
| 1 | D-Ala-OMe | (R)-2-[((1R,2S,5R)-2-isopropyl-5-methyl-cyclohexane-carbonyl)-amino]-propionic acid methyl ester | |
| 2 | D-Ala-OEt | (R)-2-[((1R,2S,5R)-2-isopropyl-5-methyl-cyclohexane-carbonyl)-amino]-propionic acid ethyl ester | |
| 3 | D-Ala-OiPr | (R)-2-[((1R,2S,5R)-2-isopropyl-5-methyl-cyclohexane-carbonyl)-amino]-propionic acid isopropyl ester | |

As shown in U.S. 20080227857 of which this application is a continuation-in-part, WS-3, WS-5, WS-12, WS-23 and WS-31, have a short duration of action (less than 1 hour) at ~10 mg/ml on the skin or slow onset (more than 5 minutes). Also, some of these compounds do not achieve significant cooling but rather produce sensations of tingling, burning, and irritation, effects that are similar to those observed with (−)-menthol, a compound with multimodal actions of sensory processes. Note that (−)-menthol is one of eight stereoisomers of menthol; it has the strongest cooling action and is the one used in commerce.

By contrast, the preferred long-acting NACE compounds deliver a perfect cooling sensation, with rapid onset, long duration of action, and minimal skin or eye irritation that has not been previously recognized.

The potency, duration, and selectivity (absence of irritation) of action are increased for the alanine derivative with the α-carbon in the D-configuration. Surprisingly, the alanine derivatives with the α-carbon in the L-configuration are virtually inactive when tested on the mucous membranes of the ocular and pharyngeal surfaces. Thus, in a racemic mixture it is estimated that about ~95% of the cough suppressant activity is contributed by the D-enantiomer.

Due to their prolonged activity, the compounds, compositions, and articles may be used therapeutically, for example, to reduce discomforts associated with pathophysiological manifestations of injury and inflammation on mucous membranes of the upper respiratory surfaces of the body.

These compounds may be delivered into the oral cavity to counteract irritation, itch and pain in therapeutic situations where prolonged relief of sensory discomfort is desired such as coughing and pharyngitis (sore throat).

These compounds inhibit the perception of itch, pain, and discomfort from the mucous membranes of the oral cavity and upper respiratory tract, and so can be used in the inhibition of sensory disorders in these tissues.

These compounds (for example, when formulated in an orally disintegrating tablet (ODT) at unit doses of up to 10 mg) have rapid onset of less than 1 minute, soothe the throat, and have potent action anti-tussive action exceeding several hours, with no irritation to the lining of the mouth and oropharynx.

Currently, there are no topical medications approved in this category for therapeutic relief of cough, although the demand exists for such substances. The potent D-Ala derivatives of Formula 1, with selective cooling and refreshing actions increase the scope of agents that may be used in the oral cavity and upper respiratory tract and may be incorporated into therapeutics such as anti-tussive and anti-asthmatic formulations.

The specific D-configuration of the α-carbon in Ala that confers the desired properties of increased potency and the presence of refreshing cooling without irritation were unexpected and surprising and not known in the prior art.

Non-Technical Description of Inventive Concept

The inventor has identified molecules with potent and prolonged activation of the perfect cool. These molecules are qualitatively and quantitatively unlike (−)-menthol and WS-3 which act for less than 20 minutes. In cough, it was observed that these NACE compounds exerts prolonged anti-nociceptive activity when the sensations of the perfect cool no longer reach conscious perception, and that repeated applications of the NACE compounds can silence and extinguish nociception. These results suggest that the perfect cool may further modulate and attenuate the plasticity of the nociceptive process.

The long-acting NACE compounds are active in cough at single doses of 1 to 10 mg or at concentrations of 10 mg/mL or less when delivered topically to the lower retropalatal oropharyngeal (LRO) surface of the pharynx.

The long-acting NACE compounds have a rapid onset of action (from about 0.5 to about 3 minutes). The onset and offset of actions of these compounds were first revealed by testing on the facial skin of subjects and then subsequently by applying them into the oral cavity, especially onto the doral surface of the tongue such that delivery of the dissolved substance (in saliva) reached the surfaces of the oropharynx. The ideal mode of delivery is via an orally disintegrating tablet.

Pharmacology and Mechanisms of Action of N-Alkylcarbonyl-Amino Acid Esters in Counter-Acting Cough Coughing is a familiar human experience and is executed by a coordinated contraction of the respiratory muscles against a closed glottis. The sudden opening of the glottis results in an explosive outburst of air and this air flow is designed to remove sensory irritants and obstructions from the airways. Thus, cough is a protective reflex. The sensations that lead to cough are multi-factorial and include conditions such as airway infections, allergies, inflammation of the airways from pollutants, pharyngitis, laryngitis, and from chronic conditions such as asthma, chronic obstructive lung disease, gastroesophageal reflux disease, lung cancer, pneumonia, pulmonary edema, and congestive heart failure.

The "urge to cough" can be modulated by the brain. For example, individuals can voluntarily suppress cough during a concert or opera. Alternatively, the ability to control cough decreases during the night when sensory inputs to the brain are diminished and the perception of the stimuli for cough is amplified. The individual then coughs more as a result.

The throat is a loose anatomical term describing the region of the body around the voicebox. Internally, an important structure for cough is the lower pharynx. The pharynx is divided into three regions: naso, oro and laryngo. The oropharynx is especially a busy traffic zone as everyday for the adult an average 12,000 L of air and 2 kg of food pass through, and it is essential for survival that the traffic flow is correct and food does not go into the airways. The swallow reflex and the cough reflex protect the airways against solid particles. The narrowest point of the traffic zone is called the lower retropalatal oropharynx (LRO) and has a cross-section of about 1 $cm^2$.

I believe that a compound of this discovery (Formula 1) delivered to the LRO via a rapid orally disintegrating tablet (ODD is an effective drug method for the treatment of cough.

The neurophysiological mechanisms of drug action is based on sensory signals that indirectly "gate" the perception of noxious stimuli that otherwise elicit the sensations for and the urge to cough. The afferent cooling signal from the oropharynx is mainly via the 9th cranial nerve (glossopharyngeal nerve) and the cough signals, thought to originate from the pharyngeal, laryngeal, oesophageal, and bronchial epithelium, may be carried by the 5th, 9th, and 10th cranial nerves. For the ODT cough tablet, it is believed that the mechanism of action is for the cooling signals from the nerve endings of the orpharynx to enter into the brainstem via the 9th nerve and then "gate" the irritant cough signals coming into the brainstem from the other cranial nerves.

I believe the concept of a ODT, containing a robust cooling agent delivered to the LRO for the pharmacological management of cough, is relatively new and such a concept has not been described in the scientific literature. The three drugs commonly used for treating cough are dextromethorphan, codeine, and menthol. Sedative antihistamines, local anesthetics, mucolytics, benzonate, and sugar solutions such as honey are also used. All of these methods in practice do not have ideal properties because they either have side-effects, slow onset, or do not work better than placebo when tested in controlled double-blind trials. No new medications for cough have been introduced in the past fifty years. Current medications for coughing have limited efficacy, as witnessed by individuals who stay awake at night, unable to sleep because of cough, and individuals who cough for prolonged periods, for example, for 3 weeks after a viral infection of the upper airways. There is need for a new medication, simply applied, that is not invasive on brain chemistry, and which will control cough for at least three to four hours to allow the individual to stop coughing and go to sleep.

The formulations of a ODT for drug delivery are known to those skilled in the art (for example, (see Reddy et al. Rapidly disintegrating oramucosal drug delivery technologies. Pharmaceutical Development and Technology 14: 588-601, 2009). Rapid orally disintegrating tablets are defined by the Food and Drug Administration (U.S.) as "A solid dosage form containing medicinal substances, which disintegrates rapidly, usually within a matter of seconds, when placed upon the tongue." Further refinement of this definition states that the tablet dissolves in the saliva and disintegrates in vitro or in vivo in 30 sec or less, and "The products are designed to disintegrate or dissolve rapidly on contact with saliva, thus eliminating the need for chewing the tablet, swallowing an intact tablet, or taking the tablet with water (Guidance for Industry: Orally Disintegrating Tablets. FDA-Center for Drug Evaluation and Research, April 2007)." Examples of such ODT formulations are sold as OTC products, for example, Sedalia®(for stress) and Sabadil® (for allergy) by Boiron®. Here the excipients are lactose, croscarmellose sodium (carboxymethylcellulose), and magnesium stearate and individual tablets are stored in blister packs and each weigh 240 to 260 mg. As contemplated here, however, smaller ODT weighing 60 to 150 mg are sufficient to achieve control of excessive cough.

The ODT, as known to the art, is designed for rapid delivery of an active ingredient into the bloodstream and hence to deliver the drug to target receptors distant from the site of application (e.g. as in anti-migraine and anti-psychotic drugs). As conceptualized here, however, the ODT is a means for localized topical delivery to the pharyngeal epithelium of the LRO.

The formulated ODT tablet described and tested in the Studies weigh 60 to 100 mg and dissolves in saliva within 15 seconds after application to the dorsal surface of the tongue. The onset of cooling action occurs in about 0.5 to 3 minutes. The duration of cooling sensation is about 15 to 30 minutes, but the anti-cough actions last for several hours.

Limitations of Menthol Lozenges in the Treatment of Cough

The public is familiar with menthol cough drops (also called lozenges or troches). No placebo-controlled studies have been published to demonstrate the effectiveness of menthol lozenges in the treatment of cough.

The neuropsychological mechanisms underlying the refreshing cooling of (−)-menthol are not understood. Sensations can be "confusing" when a chemical affects more than one sensory modality. This is especially true for (−)-menthol (also known as l-menthol, (1R)-menthol, and (1R,2S,5R)-menthol). Menthol is widely used as a cooling agent but it has multimodal action on sensory processes. For example, in the upper airways and oral cavity, menthol can elicit somatosensation (cooling, irritation, tingling), olfaction (minty), and gustation (bitter). As a counter-irritant, menthol can briefly reduce irritation of oral and pharyngeal membranes (e.g., strong mints or toothpastes) and have analgesic actions on muscle (e.g., BenGay® ointment). The multimodal actions of menthol may further mix to give rise to complex perceptions of irritation (burning, prickling, stinging), especially around the eyes, of thermal effects (cooling, warming) and of tactile effects (buzzing, tingling, tickling, numbing). In the nose and oral cavity, the predominant mode of detecting menthol is olfactory (see, e.g., Nagata et al., J. Exptl. Psychol., 31: 101-109, 2005). The strong cooling sensations of mint candies such as Mentos in the nasal cavity come from retronasal delivery of volatilized menthol in the breath onto nasal membrane receptors.

A lozenge is defined as a hard candy, some with a glycerinated base and mucilage, and "slowly dissolving" in the mouth to release the active ingredient (Remington the Science and Practice of Pharmacy, 21st Edition, 2005, pg. 925). Menthol lozenges or cough drops typically weigh about 2.7 g (N'Ice lozenges) to 3.4 g (Walgreens cough drops) and contain from 5, 7, or 10 mg of (−)-menthol in a sugar-dye matrix. Higher doses of menthol cannot be used because it becomes irritating and unpleasant. The lozenges are held in mouth for at least 10 to 15 min, have a harsh taste, add sugar calories to the diet, but exert some cooling and soothing action on the back of the throat. Thus, a lozenge as a drug delivery vehicle, is clearly different from an ODT.

In my experience of testing an ODT containing 5 to 10 mg of (−)-menthol, I found a short cooling action, lasting less than 10 minutes. The sensation can be initially localized to the pharynx but, at higher doses of 10 mg or more, coolness rapidly extends to the upper chest, most likely as a result of the distribution of the (−)-menthol into the esophagus. This cooling sensation of the chest, felt along the sternum, can be uncomfortable. (−)-Menthol, has a smaller molecular weight than the compounds of this discovery (156 Daltons vs ~250+ Daltons), and is known to distribute rapidly away from its site of application. Menthol, because of its volatility, cannot be readily formulated into orally disintegrating tablets.

Currently available cooling agents, such as menthol and WS-3, approved for use in confectionery, do not have sufficient duration of action on the LRO to be therapeutically valuable in the treatment of cough. In order to treat cough, a compound must an anti-tussive action for at least one hour and preferably longer, otherwise the patient would have to repeatedly apply the drug to obtain relief. For an anti-irritant or anti-tussive action in the pharynx/airways, the ideal agent should have rapid onset of action, soothing effects, and the ability to relieve discomfort for an extended duration, for example, at least several hours. There must be a "wow effect" of the active ingredient to stop the cough. This is achieved by the compounds of Formula 1 of this discovery.

Bioassays of N-Alkylcarbonyl-Amino Acid Esters (NACE)

Psychic events such as refreshment, soothing, cooling, irritation, itch, and pain cannot be verbalized by animals (animals cannot say "it feels cold", "ouch", or that "it itches"). Hence, the sensory effects of chemicals in animals must be indirectly inferred. Receptor assays, based on cells transfected with the genes for proteins associated with thermosensation (e.g., TRP-M8, TRP-A1, TRP-V1) may be used as a model of sensory processes and provide quantitative data. Here we compared D-Ala-OEt (No. 2 in Table 1) to L-Ala-OEt in a TRP-M8 assay (data from Prof. D. Bautista's laboratory at the University of California at Berkeley) and found $EC_{50}$ of 0.5 µM and 18.0 µM, respectively. The in vitro assay gives no information on onset and offset of action, but yields information on comparative potency of the two enantiomers. Further evaluation of the pharmacological properties of the test substances were based on direct tests in human subjects.

Watson et al. (U.S. Pat. No. 4,178,459) tested the properties of N-substituted p-menthane carboxamides on volunteers by putting filter paper (1×1 cm), impregnated with a known amount of compound, onto the dorsal surface of the tongue of the test subject. After 30 seconds, the subject was required to report presence or absence of a cooling effect. These data were reported as "Threshold, μg" and refer to the threshold amount of the test substance that produces cooling sensations upon application onto the tongue of a panel of human volunteers. The average threshold of (−)-menthol for 6 subjects was 0.25 μg, but there was a 100-fold variation in individual sensitivity. As noted above, coolness signals detected from the dorsal surface of the tongue may be confounded by gustatory, olfactory, and other variables, as well as by dilution from saliva.

It has been found that, if the goal is to find a drug useful for topical application onto the oropharynx for the treatment of cough, the refreshing cooling and sensory properties of a long-acting NACE compound may be first identified by dissolving a test substance in an ointment (usually Aquaphor®, which is 41% petrolatum, and the rest mineral oil, ceresin and lanolin alcohol) and singly applying the ointment (40 to 70 mg) onto the skin surface using a plastic stick. A reliable place for topical application is the skin above the upper lip (above the vermilion border of the lips), on the philtrum, lateral to the philtrum until the nasolabial folds, and on the lower nostrils (subnasale). This part of the face is known to be densely innervated with cold receptors, second only to the surfaces of the eyeball and anogenitalia. At this locus, tingling, cool and cold sensations in the skin may be experienced and rated for time of onset and intensity.

The intensity of the subjective skin sensation is rated as 0, 1, 2 or 3 with: 0 as no change; 1 as slight coolness, cold, or tingling; 2 as clear-cut signal of coolness, cold, or tingling; and 3 as robust cooling or cold. The intervals for recording sensations are 5 to 10 minutes, until two successive zeroes are obtained. The results (shown in FIG. 1) are averaged values of 4 to 6 separate trials in the same individual. The data are plotted using SigmaPlot® (Systat Software, Point Richmond Calif.) and a smoothing function with a negative exponential was used for analysis and statistical fit of the results. Confirmatory trials of cooling action of the long-acting NACE compounds were obtained in 2 to 4 individuals but not quantified for some because of the large number of chemicals that were evaluated.

The onset of drug action is taken as the time to reach 2 units of coolness intensity, and offset of drug action is the time when coolness intensity drops below 2, after previously surpassing 2 units. The duration of cooling action is defined as the offset time minus the onset time. An inactive compound is defined as one that does not exceed 2 units of cooling for 5 minutes after application. The quality of the sensation is noted, for example, as pure refreshing coolness, or if the sensation is accompanied by irritation (stinging or burning). The quality of the sensation is not rated for intensity.

It has been found that an effective method for testing a compound for effects in the oral cavity is to take a 1 to 5 mg sample and place it on the dorsal surface of the tongue, ⅔ posterior from the tip and in the midline. The subject is instructed to close and hold the substance in the mouth for at least 10 seconds and not to swallow. The description of sensations is then recorded at 5 to 10 minute intervals.

I have further refined the bioassay method for the evaluation of compounds for anti-cough activity on upper pharyngeal irritation using chili pepper sauce as the cough challenge with the goal of finding an effective ingredient in the treatment of cough. This method is further described in Bioassay Procedures and in Study 1.

Qualitative Aspects of Cool and Cold Intensity

The long-acting NACE compounds described herein are useful as a topical agent for the relief of sensory discomfort, and mimic the effects of running cold water on injured skin. The "nominal" ambient skin surface temperature to mimic with a cooling agent is in the range of 15 to 22° C. The effect can also be simulated by putting a towel wet with water at room temperature onto the face. The coolness of a wet towel will rapidly dissipate, an effect called adaptation, even when the cooling stimulus is still there. On the other hand, for a chemical agent the duration of cooling is more persistent. The exact physiological sensation to replicate with the inventive compounds is that of refreshing, soothing coolness, with minimal or no sensations of irritation or sting, and the absence of excessive cold.

As shown in the Studies, the preferred long-acting NACE compounds, were first identified by testing on the facial skin at ~10 mg/ml. The compounds of interest were those with a perfect cool and a rapid onset of action (less than 5 minutes) and slow offset (more than 1 hour). By contrast, various structurally similar compounds were either inactive or had a short duration of action, as shown by comparative data in FIG. 1 and in the Studies.

The long durations of action of some preferred NACE compounds were unexpected and surprising. The ability of the compounds of Formula 1 to leave a lingering "memory trace" to suppress cough was unexpected.

On the tongue of normal subjects, the effects of a NACE compound may elicit an initial "tickle" of 1 to 3 seconds, then the onset of robust and refreshing cooling could be detected. Usually, at a dose of 1 to 2 mg of a NACE compound, such as the D-Ala-OMe or D-Ala-OEt analogs, the cooling sensations lasted for about 30 minutes. Surprisingly, in subjects with cough or irritative stimuli originating from the throat, there was rapid (within 1 minute) attenuation of sensory discomfort and the cessation of coughing. Also surprisingly and unexpectedly, the duration of the anti-tussive effect lasted for at least several hours and occurred when the cooling sensations were no longer detected in the oral cavity. This soothing effect on the oropharynx and throat was especially beneficial to two asthmatic subjects who had frequent cough, chest tightness, and wheezing.

Use of Long-Acting NACE in Cough and Airway Irritation

The sensations of stimuli that initiate cough and the physical act of coughing represent the body's response to airway irritation and obstruction. The causes of airway irritation and obstruction are multifactorial and include upper airway infections, post-nasal drip, allergies, inflammation of the airways from irritants, pharyngitis, laryngitis, and chronic conditions such as asthma, chronic obstructive lung disease, gastroesophageal reflux disease, lung cancer, pneumonia, pulmonary edema, and congestive heart failure. It has been found that the NACE compounds gate and over-ride signals of airway irritation and obstruction and thus attenuate the sensations of stimuli that initiate discomfort in the throat, for example, from pharyngitis (sore throat) and laryngitis (hoarseness and loss of voice). The desire to cough is blunted and the frequency of coughing is reduced. The sense of airway obstruction, however, is not affected and voluntary coughing can be readily initiated to clear the obstruction.

A descriptor of the actions of the long-acting NACE compound of Formula 1 in cough would be as a "cough antagonist" and not as a "cough suppressant" because the ability of the individual to cough is not suppressed. Instead, the NACE compound is soothing the irritative sensations that initiate involuntary coughing. The site of NACE compound action is most likely on sensory nerve endings of the glossopharyngeal nerve in the oropharynx. The afferent signals to the brainstem then "gate" or attenuate the irritative signals for cough coming in from the afferents of the laryngeal branch of the vagus and other cranial nerves. The net effect is that the cough signals are no longer perceived as irritating or sufficient to initiate the cough reflex.

When used in the treatment of other upper respiratory disorders, the long-acting NACE compound may be used in combination with a β-adrenoreceptor agonist such as formoterol, an anti-inflammatory glucocorticosteroid such as betamethasone, or a muscarinic receptor antagonist such as ipratropium or tiotropium.

Use of Long-Acting NACE to Limit Viral Transmission in a Flu-Epidemic

Methods for controlling influenza epidemics are limited to strategies such as vaccines, isolation of infected individuals (quarantine), and the use of neuraminidase inhibitors. Viruses are shed from the infected host via expectoration of large particles, droplets, and inhalable-sized materials. Sneezing is not a characteristic sign of flu, but coughing occurs frequently. A sore throat and cough usually begins 3 days after infection and cough may persist for 3 weeks.

In a quantitative model for estimating risk of infection from respirable pathogens, Nicas et al. (J. Occupational and Environmental Hygiene 2: 143-154) showed that the potential for infection from airborne pathogens is directly correlated to cough frequency. It has been found that a single individual, in an enclosed space for 4.5 hours, can infect 72% of neighbours with flu (M. B. Gregg. The epidemiology of influenza in humans, Ann. N.Y. Acad. Sciences, 353: 45-53, 1980). This sick individual was described as having a "dry, brassy cough."

Use of a potent NACE compound as a cough suppressant to reduce virus dissemination and transmission in an influenza epidemic is a new concept. It may be especially useful to help protect health workers who treat infected individuals. Cough inhibition may be a general method to limit viral infections, for example, as might occur in schools, hospitals, or other areas of crowding. This method of restricting contagion and spread may also be applied to pathogenic respiratory viruses such as respiratory syncytial virus, rhinovirus, and coronaviruses.

Use in Long-Acting NACE Smoking Cessation Therapy

Mentholated tobacco brands represent approximately 25% of the cigarettes sold in the United States. In some countries, such as the Philippines, it may be as high as 60%. Within the United States, 69% of African-Americans and 22% of Whites smoke mentholated cigarettes. The ethnic disparity in menthol preference is attributed to deliberate marketing of the cigarettes to sub-populations with the message that mentholated cigarettes are: (a) healthy and medicinal, (b) cool, clean, crisp, fresh, and refreshing, (c) youthful, silly and fun, and (d) ethnically specific.

In pharmaceutical methods for smoking cessation therapy, one objective is to deliver the sensations of the cigarette by a non-inhalation route, hence avoiding the toxic effects of tar and carbon monoxide in the cigarette smoke. Compounds of this invention may substitute for the menthol sensation of mentholated cigarettes by providing a prolonged refreshing feeling in the oral cavity and upper airways. Furthermore, the inventive compounds may be combined with nicotine or lobelline, or other nicotine receptor agonists, to form a product designed to both reduce the harsh taste of the nicotine, and to mimic the cooling and the central stimulant effects of a mentholated cigarette. The delivery methods may be a lozenge, chewing gum, spray, aerosol, syrup, gargle, mouthwash, film, or a candy designed for both cooling of the mucous membranes of the mouth and oropharynx and for buccal absorption of the nicotine.

Delivery to Target and Utility of N-Alkylcarbonyl-Amino Acid Esters

In formulating topical and oral compositions, the long-acting NACE compound may be incorporated into a vehicle that by itself may be inert or may contain other active ingredients.

Suitable formulations for the oral cavity and oropharynx, for example, include compositions such as liquids, powders, tablets, films, or pastes. ODT, as contemplated here, are pharmaceutical dosage forms that disintegrate in saliva within 30 sec of topical application on the surface of the tongue. A typical ODT is composed predominantly of an inert vehicle, diluent, or carrier. A medicinal agent is interspersed within this carrier. The ODT will dissolve when placed on the dorsal surface of the tongue thereby releasing the medicinal agent so that it may come in contact with the tissues of the lower oropharynx (LRO). A typical diluent, carrier, or vehicle may be a "polyhydric alcohol" construed as describing the following substances: xylitol, mannitol, sorbitol, maltitol, isomaltitol, maltotriitol, lactitol, and β-linked-glucopyranasido-sorbitol. Flavoring agents such as the sweeteners, aspartame, sucralose, or alitame, may be added to mask any tastes. The mix is granulated to a uniformly dispersed blend; dispersing agents, anti-caking agents, and lubricants may be added; and the mixture is then compressed to form the ODT.

In one test formulation used in the Studies, ODT tablets were made using Ludipress®, a direct compression excipient from BASF Chemical Corp., which is a granulated blend of lactose and polyvinylpyrrolidone. The test substance was first mixed with Ludipress® using a mortar and pestle, then suspended in an equal volume of 10%-90% ethanol-distilled water (voVvol). A disposable pipette was then used to aliquot the liquid mixture onto a sheet of wax paper and dried at room temperature. The dried tablets were then weighed and sorted. It was found by experiment that a 80 mg tablet containing 2 mg (2.5% wt/vol) of test substances dissolved within 15 seconds when placed on the dorsal surface of the tongue. A robust, refreshing cooling sensation was experienced in the LRO region that counteracted cough.

In a second formulation, the carrier was a 80%-20% mixture of mannitol-maltitol (Pearlitol™ and Sweetpearl™, Roquette Freres, France). This carrier had the advantage of completely masking bitter tastes that might be present in some of the test substances.

Summary of Experimental Results from Bioassays

The principal findings from experiments performed on the skin are summarized in Table 2. The beneficial effects of the long-acting NACE compounds are the long duration of action in the absence of significant eye irritation.

TABLE 2

Summary comparison of unique properties of long-acting NACE compounds with other compounds.

| Chemical Class | Cooling on tongue | Cooling on skin of face | "perfect" cooling experience | Eye Irritancy | Acts for >1 hour at 40 mM |
|---|---|---|---|---|---|
| Long-acting NACE | yes | yes | yes | no | yes |
| non-NACE carboxamides | yes | variable | no | yes | no |
| (−)-menthol | yes | yes | no | yes | no |
| SD alcohol | no | yes | yes | yes | no |

Chemical Synthesis of N-Alkylcarbonyl-Amino Acid Esters and Related Compounds

Many substituted amino acid esters may be obtained from commercial sources such Sigma-Aldrich Corp., St. Louis, Mo., USA. For example, β-alanine ethyl ester, and L- or D-alanine methyl ester, are listed in the 2003-2004 Aldrich Catalog. The precursor, D-alanine ethyl ester is available from Indofine Chemicals, Co., Hillsborough, N.J. The precursor, D-alanine isopropyl ester is not available from commercial sources and was custom synthesized (Phoenix Pharmaceuticals, Burlingame, Calif.; Diapharm Ltd., St. Petersburg, Russia). The acid chloride is reacted with the appropriate amino acid ester to form the NACE compound.

As an example of synthetic procedure, D-Ala methyl ester hydrochloride was obtained from Aldrich Chemical Co., 1.0 g was dissolved in 28 mL diethyether and 1 mL double-distilled water and cooled to 0° C. A pinch of the catalyst diaminopyrimidine was added. 1.62 mL of p-menthoyl chloride was then added dropwise, followed by 2 mL of triethylamine. Clumps of white precipitates appeared in the mixture, which was stirred overnight at room temperature. The precipitate was dissolved with ethyl acetate, washed with double-distilled water, and dried over sodium sulfate. The organic phase was then evaporated under reduced pressure to yield the final product (2 g), which crystallized at room temperature. The expected molecular mass was then confirmed by mass spectroscopy and the absorption spectrum by nuclear magnetic resonance.

Bioassay Procedures
Cooling on Skin

For bioassay on the skin, approximately 30 mg was stirred and dissolved in 3 g of warm liquid Aquaphor® ointment to a yield a 40 mM (~1% wt/vol) ointment. The exact amount was adjusted so that the molar equivalent was about 35 to 40 mM. After cooling, 40 to 70 mg of the solid ointment was placed on the tip of a plastic stick and applied to the skin above the upper lip, on the philtrum, and lateral to the philtrum, up to the nasolabial folds, of test subjects and the onset and duration of cooling sensations noted.

The intensity of the subjective skin sensation was rated as 0, 1, 2 or 3 with: 0 as no change; 1 as slight coolness, cold, or tingling; 2 as clear signal of coolness, cold, or tingling; and 3 as robust cooling or cold. The intervals for recording sensations were 5 to 10 minutes, until two successive zeroes were obtained. The results (shown in FIG. 1) are averaged values of 4 to 6 separate trials in the same individual. The data are plotted using SigmaPlot® (Systat Software, Point Richmond, Calif., USA) and a smoothing function with a negative exponential was used for analysis and statistical fit of the results.

The onset of drug action was taken as the time to reach 2 units of coolness intensity, and offset of drug action was the time when coolness intensity drops below 2, after previously surpassing 2 units. The duration of cooling action was defined as the offset time minus the onset time. An inactive compound is defined as one that did not exceed 2 units of cooling after application. The quality of the sensation was also noted: such as pure refreshing coolness, or if the sensation was accompanied by irritation (stinging or burning). The quality of the sensation was not rated for intensity.

Anti-Cough Activity

A number of cough challenge methods have been devised for evoking the cough reflex (Morice et al. Briti. J. Clin. Pharmacol. 52: 365-375, 2001). Usually, citric acid or capsaicin is delivered via the inhalation route to volunteers and the number of coughs counted. I have found that the sensations in the lower pharynx associated with the urge to cough can be replicated by placing (with a syringe or a plastic stick) 0.2 to 0.25 ml of a chili pepper sauce onto the posterior dorsal surface of the tongue. The chili pepper sauce used here is called Yank Sing® Chili Pepper Sauce (YS Gourmet Productions, Inc., PO Box 26189, San Francisco, Calif. 94126) and is a well-known condiment for use with dim sum (Chinese tea lunch). The sensations associated with the chili pepper sauce are located in the back of the mouth and are clearly recognized and associated with a desire to clear the throat.

The chili-pepper sauce evoked sensations can be readily suppressed with a drink of ice cold water or with an ODT containing a cooling ingredient, but is not affected by an ODT containing only the excipient. To test for anti-cough activity the ODT with the test substance is first administered onto the dorsal surface of the tongue and 45 to 50 min afterwards the chili-pepper sauce test is administered. If there is no attenuation of the challenge stimuli, the score is 0, if there is partial inhibition, the score is +, and if there is complete attenuation of the cough signal, the score is ++. In the presence of an ODT that results in a ++ score, the irritative signals are completely absent, yet the salty taste used in the soy sauce of the condiment can still be easily tasted. The test substances in the ODT that produced a ++ score were then identified and further tested for effectiveness in the treatment of cough.

To further document the activities fo the test molecules, the results from an eye wipe test was included. Here the test substance is applied to the closed eyelids with a towelette at a concentration of 1 mg/ml in 5%-ethanol-95%-distilled water vol/vol and the duration of cooling on the ocular surface was recorded. Surprisingly, a good correlation was found between ocular cooling duration and anti-cough activity and less so with the duration of cooling based on the philtrum skin assay. It is likely that the mucous membranes that line the ocular surface and the pharynx have similar sensory mechanisms that are somewhat different from the philtrum skin which is keratinized.

Study 1

A number of compounds were tested (see U.S. 20080227857). Some of these results (FIG. 1) show the duration of cooling (in hours) for five compounds (in order, left to right): WS-3, (−)-menthol, WS-5, D-Ala-OMe, and D-Ala-OEt. The known agents in commerce, e.g., (−)-menthol, WS-3, and WS-5, are active for ≦0.5 hr, and relatively short compared to the D-Ala-OMe and D-Ala-OEt analogs of >1.5 hr. The presence the D-Ala configuration increases duration of action (see Table 3) and these two compounds are examples of the preferred embodiments of this invention. The long-acting NACE compounds, D-Ala-OMe, D-Ala-OEt, and D-Ala-OiPr esters have a refreshing cool, without skin or eye irritancy, and are of special utility in cough.

In the results of FIG. 1, the test compounds were singly applied to the skin above the upper lips as a ~1% wt/vol (10 mg/ml) ointment. Subsequently, for the results shown in Table 3, the test dose on the philtrum was reduced to a 0.5% wt/vol (5 mg/ml) ointment. The reason for choosing a lower dose was to increase the number of trials per individual and to have a reduced chance of substances accumulating in the skin.

The data of Table 3 confirm FIG. 1 that the D-Ala analogs have the effect of increasing potency and duration of action relative to other cooling congeners. Also, these D-Ala enantiomers, in addition to selective refreshing coolness with the absence of tissue irritation when applied to the skin, also cool the ocular surface, and suppress the cough sensations evoked by chili pepper sauce applied to the pharyngeal surface. The active compounds in the suppression of cough are those of Formula 1.

Surprisingly, the L-Ala analogs: namely, L-Ala-OMe, L-Ala-OEt, L-Ala-OiPr, L-Ala-OnPr, and L-Ala-OnBu, were virtually devoid (<5%) of cooling activity on the ocular surface and on the pharyngeal surface (as a model of anti-cough activity). Thus, the D-configuration of the α-carbon of Ala is an absolute requirement for therapeutic utility in cough. This separation of activity between the D- and L-enantiomers was also apparent in the TRP-M8 receptor assay (data from Prof. D. Bautista's laboratory at the University of California at Berkeley). The $EC_{50}$ of D-Ala-OEt (No. 2 in Table 1) versus L-Ala-OEt was 0.48 μM and 18.0 μM, respectively, a difference of 37-fold. Thus, in an equal mixture (racemic) of D-Ala and L-Ala enantiomers, it is likely that ~97% of the anti-cough activity would be contributed by the D-enantiomer (of Formula 1).

The correlation of activity among the in vivo bioassay endpoints depended on tissue characteristics. Thus, activity on the philtrum assay did not precisely predict activity on the ocular surface/pepper-sauce assays. For example, the D-Ala-OnPr and D-Ala-OnBu have a long duration of action on the philtrum skin, but this is not matched by increased potency on the ocular surface or on the pepper-sauce assay. On the other hand, the eye wipe test is highly correlated to activity on the pharyngeal surface. The differences in response may be due to differences in tissue architecture and sensory mechanisms. The ocular and pharyngeal surfaces are mucous membranes, but the philtrum skin is keratinized.

One unusual feature noted in the pepper-sauce assay and in the use of ODT on cough in human subjects is that the cooling action on the oropharynx lasts about 10 to 15 min, yet the antitussive effects lasts for 3 or more hours. This "memory trace" action is most unusual, but may be explained if it is clearly recognized that the antitussive action is indirect, acting via a gating mechanism. There is no direct drug action of the cooling agent on cough receptors in the airways; that is, the cough signals are not impeded. It is the cooling Aδ/C-fiber transmitted sensory signals that are triggering release of an inhibitory process (perhaps via metabotropic glutamic acid receptors) that is gating the cough signal. The gating mechanism in the central nervous system may desensitize, hyperpolarize, or otherwise modulate the sensitivity of central neurons for an extended period of time. That is, there is a lingering memory trace in the brain that attenuates the sensations of and/or the urge the cough and that is why an antitussive effect persists in the absence of perception of the cooling sensation.

To describe this idea in lay terms, I use the analogy of going out into the spring sunshine for 15 min, being happy, and then coming back indoors. Although the skin is no longer warm after leaving the sun, the change in mood may last for several hours or longer. A pleasant cooling memory trace may thus reduce sensitivity to noxious stimuli (W. Wordsworth describes the power of a memory trace as: "They flash upon that inward eye, Which is the bliss of solitude; And then my heart with pleasure fills, And dances with the daffodils.")

TABLE 3

Bioassay results of substances applied to the philtrum skin in an ointment vehicle, to the eylids with a towelette, and in response to a cough challenge. The test concentrations for the philtrum was 5 mg/ml in Aquaphor ® ointment and the concentrations for the eye wipes was 1 mg/ml in 5%-95% v/v ethanol-distilled water. The duration of cooling is recorded as (minutes). In the chili-pepper sauce cough challenge test, the challenge was applied 45 to 50 min after the ODT which contained 2 mg of the test subsance, and ++ indicates the ability of the test substance to suppress the cough sensations elicited by the pepper sauce.

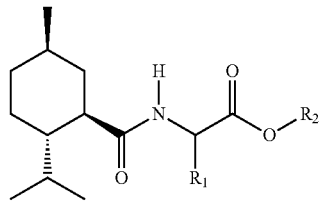

Note: this diagram is different from Formula 1, and includes Gly esters

| Compounds | $R_1$ | $R_2$ | Philtrum Skin (min) | Eyelids/Ocular Surface (min) | Chili-Pepper Sauce Test |
|---|---|---|---|---|---|
| Gly-OEt (WS-5) | H | Et | 24 | 15 | 0 |
| Gly-OnPr | H | nPr | 42 | 54 | 0 |
| Gly-OnBu | H | nBu | 38 | 35 | 0 |
| D-Ala-OMe (*, 1) | Me | Me | 77 | 120 | ++ |
| D-Ala-OEt (*, 2) | Me | Et | 103 | 180 | ++ |
| D-Ala-OiPr (*, 3) | Me | iPr | 34 | 360 | ++ |
| D-Ala-OnPr | Me | nPr | 108 | 65 | + |
| D-Ala-OnBu | Me | nBu | 80 | 40 | 0 |
| L-Ala-OMe | Me | Et | 25 | 10 | 0 |
| L-Ala-OEt | Me | Et | 34 | 0 | 0 |
| L-Ala-OiPr | Me | Et | 27 | 15 | 0 |
| L-Ala-OnPr | Me | Et | 22 | 10 | 0 |
| L-Ala-OnBu | Me | Et | 0 | 0 | 0 |
| D-NMeAla-OEt | Me | Me | 0 | 0 | 0 |

(*, no.) denote compounds that fulfill the criteria of being a long-acting NACE compound for anti-cough applications. The structures correspond to No. 1, 2, and 3 of Table 1, respectively.

Study 2

The compounds of Formula 1 are white crystalline solids at room temperatures. These compounds were tested as the pure powder (>95% purity, by HPLC analysis), or mixed 1:1 with powdered or granulated sugar. The test substances were applied at 2 to 5 mg on the mid-point of the dorsal surface of the tongue using a metal spatula or a plastic applicator. After depositing the test substance on the tongue, the subject was instructed to keep the mouth closed and allow the fluids of the mouth to inter-mix with the test substance and to distribute it to the back of the mouth (oropharynx). The presence and duration of subjective sensations from the mouth was then recorded. In the oral cavitiy, robust cooling actions of the D-Ala analogs of Formula 1 were noted. WS-3 and WS-23, both without the D-Ala steric configuration, also had cooling properties at the same dose, but the duration of action was shorter, less than 10 minutes, and there was some sensory irritation with these compounds.

Study 3

Two males, both aged 60 years, were inveterate cigar smokers consuming 3 to 5 cigars per day. They both had frequent bouts of dry, non-productive, hacking coughs. At night, there were episodes of insomnia characterized by difficulties in breathing, an oppressive pressure on the chest and throat, and subsequent awakening with sensations of choking. During the day, a frequent and persistent sensation was that of tickling, irritative feelings in the back of the throat that led to coughing.

In 20 trials, 10 trials per subject, two mg of 95%+ pure powder of a D-Ala ethyl compound (No. 2 in Table 1, (R)-2-

[(((1R,2S,5R)-2-isopropyl-5-methyl-cyclohexanecarbonyl)-amino]-propionic acid ethyl ester)) of Formula (1) was placed on the mid-portion of the tongue of these two subjects. Both subjects reported relief from the desire to cough within 1 minute after application. Sensations of robust coolness in the back of the throat was noted and lasted for about 30 minutes. Applications of similar amounts of powdered sugar were not effective. The placebo could be clearly distinguished from the active compound because of the absence of cooling sensations.

After application of test substance, the absence of irritation and itching at the back of the throat (cough signals) lasted for about 4 to 5 hours and the individual was observed not to cough for 6 to 8 hours. Surprisingly, after 4 applications in one individual and after 6 applications in the second individual, within a period of 2 days, the individuals noted that the desire to cough was removed for at least 5 days, in spite of continued smoking of cigars. This suggested that the test compound may have down-regulated the cough receptor mechanisms and permanently raised the threshold for cough stimuli. This therapeutic effect occurred when the test substance no longer elicited cooling sensations in the oropharynx.

Study 4

A 61-year old female with a documented 31-year history of asthma attacks volunteered to test one of the compounds falling within Formula (1). She was extremely sensitive to agents such as tobacco smoke, dust, pollen, odors, down/woolen materials, house cleansing products, pets, and sudden change of air temperature, and reacted with violent coughing, mucus secretions, wheezing, choking, and shortness of breath. At the time of this trial, she was taking these medications for her condition: theophylline, Allegra®, Advair®, Intal®, and Singulair®. In 5 trials, during a coughing spree, she placed one to two mg of 95%+ pure powder of a D-Ala ethyl ester (No. 2 in Table 1, ((R)-2-[((1R,2S,5R)-2-isopropyl-5-methyl-cyclohexanecarbonyl)-amino]-propionic acid ethyl ester))) of Formula (1) on the mid-portion of her tongue. She reported a soothing and cool sensation with a slight taste similar to Eucalyptus oil in her mouth and throat. Coughing stopped after 3 to 5 minutes and breathing was normal. She did not sense any build up of mucus or other side-effects. In three trials when the compound was applied at night, she slept through the night without being awakened by cough. Her husband remarked that, in over 30 years of marriage, this was the first time that he had seen an effective medication for her cough. She noted that the irritative signals of cough were absent in the presence of the applied chemical, but she still sensed a mechanical build up of secretions in her airways and could voluntarily cough up such secretions if necessary. She continues to use the test compound for management of her asthma, with the knowledge and consent of her physician. Surprisingly, her asthmatic coughing attacks have not recurred with any severity for one month. This effect suggests that one of the pathophysiological signs of asthma, airway hyper-reactivity, may be attenuated by the treatment.

Study 5

A 74-year old male had adult-onset asthma for 20 years. Triggers for attacks were tobacco smoke, dust, and changes in air temperature. He used Foradil® (formoterol fumarate) and Asmanex® (mometasone fuorate) twice a day to control his asthma, and monitored his pulmonary function with a portable device for measuring peak expiratory flow. He had daily episodes of both productive and non-productive cough. In 5 trials, when he felt throat irritation and a desire to cough, placement of 1 to 3 mg of (R)-2-[((1R,2S,5R)-2-isopropyl-5-methyl-cyclohexanecarbonyl)-amino]-propionic acid ethyl ester) (No. 2 in Table 1) provided rapid relief and was described as soothing and removed "tightness" in the chest. Peak expiratory flow improved from 320 Umin to 370 Umin. In 3 episodes where the test substance was administered in the midst of a productive cough spell, no significant effects were observed and the subject said that the applied compound had been expectorated. The subjective response to the long-acting NACE compound was definitely favourable. The subject remarked that the best time to use the NACE compuound was after inhaling the crystalline Foradil® because this inhaled drug irritated his throat. Menthol lozenges were not effective for his airway discomfort because they only had mild anti-irritant actions and the sugar content of the lozenges interfered with his appetite for food.

Study 6

ODT containing 2.0 to 2.5 mg of D-Aa Me Ester, D-Ala Et Ester, or D-Ala iPr Ester (identified chemically in Table 1 as No. 1, No. 2, and No. 3, respectively) were prepared using mannitol/maltitol as the excipient and stored in tic-tac boxes each containing 10 tablets. Over a course of two years, 14 adult males with cough tested these tablets. The causes of coughing were colds/flu, allergies, pharyngitis, excessive smoking, and two cases of gastroesophageal reflux. These individuals all had advanced degrees (M.D. or Ph.D.) and were motivated to try the tablets by scientific curiosity or because of financial interests in drug development, or, in several cases, by the annoyance caused by the cough. These subjects had no difficulties in learning how to self-administer the ODT. The ODT placed on the mid-posterior dorsal surface of the tongue disintegrated in saliva in less than 15 sec and the sensory agent was then felt to coat the lower pharynx. No adverse effects were noted. The D-Ala Me Ester, D-Ala Et Ester, and D-Ala iPr Ester ODT were readily detected because they exerted a robust cooling action on the pharyngeal surface. Placebo ODT containing the excipient alone or the D-NMe Ala Ester or L-Ala Et Ester were immediately detected as being inactive and thereby rejected after one trial. The ODTs containing the afore-mentioned active test compounds were 100% effective in reducing cough. The desired pharmacological effect was achieved in all subjects. The individual not only felt better, but the people around the subjects within 10 min noticed the absence of coughing after administration. There was no ambiguity about the ability of the ODT to reduce coughing and to counteract pharyngeal irritation in all tested subjects.

The foregoing has described the principles, preferred embodiments, and modes of operation of the present invention. However, the invention should not be construed as limited to the particular embodiments discussed. Instead, the above-described embodiments should be regarded as illustrative rather than restrictive, and it should be appreciated that variations may be made in those embodiments by workers skilled in the art without departing from the scope of the present invention.

The invention claimed is:

1. An orally disintegrating tablet comprising:
(R)-2-[((1R,2S,5R,2S,5R)-2-isopropyl-5-methyl-cyclohexanecarbonyl)-amino]-propionic acid isopropyl ester.

* * * * *